US006245831B1

(12) United States Patent
Tsai et al.

(10) Patent No.: US 6,245,831 B1
(45) Date of Patent: Jun. 12, 2001

(54) DISPOSABLE ARTICLES HAVING BIODEGRADABLE NONWOVENS WITH IMPROVED FLUID MANAGEMENT PROPERTIES

(75) Inventors: Fu-Jya Daniel Tsai; Brigitte C. Wertheim, both of Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 18 days.

(21) Appl. No.: 09/606,599

(22) Filed: Jun. 29, 2000

Related U.S. Application Data

(60) Division of application No. 09/436,365, filed on Nov. 9, 1999, now Pat. No. 6,194,483, which is a continuation-in-part of application No. 09/144,153, filed on Aug. 31, 1998.

(51) Int. Cl.[7] .................................................. C08K 7/02

(52) U.S. Cl. ........................................ 523/124; 523/222

(58) Field of Search .................................... 523/124, 222

(56) References Cited

U.S. PATENT DOCUMENTS

| 2,703,316 | 3/1955 | Schneider . |
| 3,531,561 | 9/1970 | Trebu . |

(List continued on next page.)

FOREIGN PATENT DOCUMENTS

| 4016348 | 11/1991 | (DE) . |
| 0394954 | 10/1990 | (EP) . |
| 0515203 | 11/1992 | (EP) . |
| 569153 | 11/1993 | (EP) . |
| 0765913 | 4/1997 | (EP) . |
| 5-71005 | 3/1993 | (JP) . |
| 5-140361 | 6/1993 | (JP) . |
| 6-207320 | 7/1994 | (JP) . |
| 6-207323 | 7/1994 | (JP) . |
| 6-207324 | 7/1994 | (JP) . |
| 6-248552 | 9/1994 | (JP) . |
| 7-133511 | 5/1995 | (JP) . |
| 8-134723 | 5/1996 | (JP) . |
| 8-260320 | 10/1996 | (JP) . |
| 92-04410 | 3/1992 | (WO) . |
| 94-07941 | 4/1994 | (WO) . |
| 94-08078 | 4/1994 | (WO) . |
| 95-08660 | 3/1995 | (WO) . |
| 95-17216 | 6/1995 | (WO) . |

OTHER PUBLICATIONS

Federova, R.G. et al. Chemical Abstracts 109(4)24162z, "Composite Fibers From Polyacrylonitrile–Aromatic Polyamic Acid Blends" *Khim. Volokna* 2 11–12 1998.

ASTM Designation: D 1238–95, "Standard Test Method for Flow Rates of Thermoplastics by Extrusion Plastometer," pp. 273–281 1996.

American Society for Testing Materials (ASTM) Designation: D 5338–92, Standard Test Method for Determining Aerobic Biodegradation of Plastic Materials Under Controlled Composting pp. 456–461 1993.

Slizite, G. et al. Chemical Abstracts 105(26)228372v, "Study of Photochemical Degradation of Articles Produced from Complex Triacetate–Polyamide Fiber" *Nauch. Tr. Vuzov LitSSR. Khimiya i Khim. Teknol.* 27 98–102 1986.

U, Ju Jui et al. Chemical Abstracts 106(12)86124k, "Use of a Reactively Dyed Low–Molecular–Weight Polycaproamide for Production of Colored Polypropylene Fibers" *Khim. Volokna* 6 22–24 1986.

Zhao Delu, Xue Du et al. Chemical Abstracts 105(12)99049u, "Applications of Controlled Degradation in Polyporpylene Tape Yarns" *Suliao* 15 5–10 1986.

Zakirov, I.Z. Chemical Abstracts 102(22)186548n, "Temperature Transitions in Polyacrylonitrile–Fibroin Mixtures" *Vysokomol. Soedin., Ser. B* 27 116–120 1985.

Sagatova, M. Sh. et al. Chemical Abstracts 102(10)80131f, "Structural and Mechanical Properties of Fibers Produced From Mixtures of Polyacrylonitrile and Chlorinated Poly-(vinyl chloride)" Viniti Deposited 1984 939–8 Document 4 (10 pp.).

Dreizenshtok , G.S. et al. Chemical Abstracts 99(8)54963d, "Cellulose Decomposition in the Sintering of Fibers from Poly(tetrafluoroethylen) Dispersions" *Khim. Volokna* 3 33–34 1983.

Gusev, V.K. et al. Chemical Abstracts 96(10)70305j, "Two Component Acetate Threads" *Khim. Volokna* 6 31–32 1981.

Zakirov, I.Z. Chemical Abstracts 96(4)21192M, "Effect of Small Amount of Polymeric Additives on Sturctural–Mechanical and Thermal Properties of Synthetic Fibers Spun By a Wet Method" *3–i Mezhdunar. Simpoz. po Khim. Voloknam, Kalinin, 1981, Kalinin* 5 105–110 1981.

Good, Robert J., et al. *Surface and Colloid Science–Experimental Methods* II 31–91 1979.

Fedorova , R.G. et al. Chemical Abstracts 188(16)106639x, "Structural Thermal Stabilization of Fibers Based on Aromatic and Heterocyclic Polymer Blends" *Prepr. –Mezhdunar. Simp.Khim. Voloknam 2nd* 4 36–45 1977.

(List continued on next page.)

*Primary Examiner*—Kriellion Sanders
(74) *Attorney, Agent, or Firm*—Kilpatrick Stockton LLP

(57) ABSTRACT

A disposable article including a biodisintegratable nonwoven material having improved fluid management properties. The nonwoven material may be produced using a thermoplastic composition that comprises a unreacted mixture of an aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid; and a wetting agent. The thermoplastic composition exhibits substantial biodegradable properties yet is easily processed. The biodisintegratable nonwoven materials may be used in a disposable absorbent product intended for the absorption of fluids such as body fluids.

48 Claims, No Drawings

U.S. PATENT DOCUMENTS

| | | |
|---|---|---|
| 3,792,011 | 2/1974 | Smith et al. . |
| 3,853,820 | 12/1974 | Vachon . |
| 3,921,333 | 11/1975 | Clendinning et al. . |
| 3,964,486 | 6/1976 | Blaney . |
| 4,137,921 | 2/1979 | Okuzumi et al. . |
| 4,175,177 | 11/1979 | Potts . |
| 4,367,070 | 1/1983 | Hayashi et al. . |
| 4,489,056 | 12/1984 | Himmelstein et al. . |
| 4,685,909 | 8/1987 | Berg et al. . |
| 4,710,187 | 12/1987 | Boland et al. . |
| 4,762,521 | 8/1988 | Roessler . |
| 4,770,656 | 9/1988 | Proxmire et al. . |
| 4,789,592 | 12/1988 | Taniguchi et al. . |
| 4,798,603 | 1/1989 | Meyer et al. . |
| 4,800,219 | 1/1989 | Murdoch et al. . |
| 4,931,488 | 6/1990 | Chiquet . |
| 4,959,410 | 9/1990 | Eichenauer et al. . |
| 4,983,689 | 1/1991 | Yu . |
| 5,057,368 | 10/1991 | Largman et al. . |
| 5,069,970 | 12/1991 | Largman et al. . |
| 5,076,983 | 12/1991 | Loomis et al. . |
| 5,108,820 | 4/1992 | Kaneko et al. . |
| 5,147,712 | 9/1992 | Miyahara et al. . |
| 5,160,472 | 11/1992 | Zachariades . |
| 5,162,153 | 11/1992 | Cooke et al. . |
| 5,180,765 | 1/1993 | Sinclair . |
| 5,202,178 | 4/1993 | Turner . |
| 5,223,546 | 6/1993 | Morita et al. . |
| 5,238,968 | 8/1993 | Morita et al. . |
| 5,241,066 | 8/1993 | Davis et al. . |
| 5,252,642 | 10/1993 | Sinclair et al. . |
| 5,258,422 | 11/1993 | Chang et al. . |
| 5,273,596 | 12/1993 | Newkirk . |
| 5,277,976 | 1/1994 | Hogle et al. . |
| 5,286,770 | 2/1994 | Bastioli et al. . |
| 5,294,469 | 3/1994 | Suzuki et al. . |
| 5,321,068 | 6/1994 | De Witt, Jr. . |
| 5,336,552 | 8/1994 | Strack et al. . |
| 5,338,822 | 8/1994 | Gruber et al. . |
| 5,340,646 | 8/1994 | Morita et al. . |
| 5,382,400 | 1/1995 | Pike et al. . |
| 5,405,887 | 4/1995 | Morita et al. . |
| 5,412,005 | 5/1995 | Bastioli et al. . |
| 5,424,346 | 6/1995 | Sinclair . |
| 5,434,004 | 7/1995 | Ajioka et al. . |
| 5,444,113 | 8/1995 | Sinclair et al. . |
| 5,446,123 | 8/1995 | Gruber et al. . |
| 5,462,983 | 10/1995 | Bloembergen et al. . |
| 5,475,080 | 12/1995 | Gruber et al. . |
| 5,484,881 | 1/1996 | Gruber et al. . |
| 5,489,474 | 2/1996 | Shinoda et al. . |
| 5,500,465 | 3/1996 | Krishnan et al. . |
| 5,502,158 | 3/1996 | Sinclair et al. . |
| 5,508,378 | 4/1996 | Ohara et al. . |
| 5,525,706 | 6/1996 | Gruber et al. . |
| 5,545,681 | 8/1996 | Honkonen . |
| 5,593,778 | 1/1997 | Kondo et al. . |
| 5,637,631 | 6/1997 | Kitada et al. . |
| 5,691,424 | 11/1997 | Suzuki et al. . |
| 5,714,618 | 2/1998 | Kimura et al. . |
| 5,783,504 | 7/1998 | Ehret et al. . |

OTHER PUBLICATIONS

Geleji, Frigyes et al. Chemical Abstracts 82(14)87465v, "Bicomponent Fiber Structures on Polypropylene Basis" *J. Polym. Sci., Polym. Symp.* 42, 713–716 1973 Pt. 2.

Whittington, Lloyd R. Whittington's Dictionary of Plastics p. 258 1968.

Database WPI Derwent Publications Ltd., Database WPI, EP 640474, (H. Utz), "Laminated Film Manufactured By Vacuum Deposition of Functional Layer Between Two Films" Abstract.

Database WPI Derwent Publication Ltd., Database WPI, JP 6–212511 A, (Unitika Ltd.), "Biodegradable Staple Fiber Useful for Sanitary Napkin" Abstract.

Database WPI Derwent Publications Ltd., Database WPI, JP 9–041220 A, (Unitika Ltd.), "Biodegradable Polyester Fiber" Abstract.

Chemical Abstracts 114(22)209209s: abstract of laid open Japanese patent application JP 3040865.

Chemical Abstracts 119(12)119421d: abstract of laid open Japanese patent application JP 5093316.

Chemical Abstracts 119(12)119422e: abstract of laid open Japanese patent application JP 5093318.

Chemical Abstracts 119(24)252062d: abstract of laid open Japanese patent application JP 5163616.

Chemical Abstracts 120(8)79336s: abstract of laid open Japanese patent application JP 5093317.

Chemical Abstracts 122(2)12043s: abstract of laid open Japanese patent application JP 6212548.

Chemical Abstracts 122(2)12091f: abstract of laid open Japanese patent application JP 6248515.

Derwent World Patents Database, abstract of JP 06–248551 (Kuraray Co. Ltd), "Aliphatic Polyester Based Melt Blown Nonwoven Fabric."

Patent Abstracts of Japan, abstract of JP 08–188922 (Aikawa Toshio) , "Conjugate Fiber and Fiber Sheet Using the Same."

Derwent World Patents Database, abstract of JP 04–335060 (Mitsui Toatsu Chem Inc (MITK)), "Thermoplastic and Decomposable Polymer Composition for Packaging."

DISPOSABLE ARTICLES HAVING BIODEGRADABLE NONWOVENS WITH IMPROVED FLUID MANAGEMENT PROPERTIES

CROSS-REFERENCE TO RELATED APPLICATIONS

This application is divisional patent application of U.S. patent application Ser. No. 09/436,365, filed Nov. 9, 1999 now U.S. Pat. No. 6,194,483, which is a continuation-in-part patent application of U.S. patent application Ser. No. 09/144,153, filed on Aug. 31, 1998.

FIELD OF THE INVENTION

The present invention relates to a disposable article having a biodisintegratable nonwoven material having improved fluid management properties. The nonwoven material may be produced from polymer blends. These blends may include multicomponent fibers. These multicomponent fibers comprise an unreacted mixture of an aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid; and a wetting agent. The multicomponent fiber exhibits substantial biodisintegratable properties yet is easily processed. The disposable absorbent product may be used for the absorption of fluids, such as body fluids.

BACKGROUND OF THE INVENTION

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a topsheet, a backsheet, and an absorbent structure between the topsheet and backsheet. These products usually include some type of fastening system for fitting the product onto the wearer.

Disposable absorbent products are typically subjected to one or more liquid insults, such as of water, urine, menses, or blood, during use. As such, the outer cover backsheet materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Although current disposable baby diapers and other disposable absorbent products have been generally accepted by the public, these products still have need of improvement in specific areas. For example, many disposable absorbent products can be difficult to dispose of. For example, attempts to flush many disposable absorbent products down a toilet into a sewage system typically lead to blockage of the toilet or pipes connecting the toilet to the sewage system. In particular, the outer cover materials typically used in the disposable absorbent products generally do not disintegrate or disperse when flushed down a toilet so that the disposable absorbent product cannot be disposed of in this way. If the outer cover materials are made very thin in order to reduce the overall bulk of the disposable absorbent product so as to reduce the likelihood of blockage of a toilet or a sewage pipe, then the outer cover material typically will not exhibit sufficient strength to prevent tearing or ripping as the outer cover material is subjected to the stresses of normal use by a wearer.

Furthermore, solid waste disposal is becoming an ever increasing concern throughout the world. As landfills continue to fill up, there has been an increased demand for material source reduction in disposable products, the incorporation of more recyclable and/or degradable components in disposable products, and the design of products that can be disposed of by means other than by incorporation into solid waste disposal facilities such as landfills.

As such, there is a need for new materials that may be used in disposable absorbent products that generally retain their integrity and strength during use, but after such use, the materials may be more efficiently disposed of. For example, the disposable absorbent product may be easily and efficiently disposed of by composting. Alternatively, the disposable absorbent product may be easily and efficiently disposed of to a liquid sewage system wherein the disposable absorbent product is capable of being degraded.

Many of the commercially-available biodegradable polymers are aliphatic polyester materials. Although fibers prepared from aliphatic polyesters are known, problems have been encountered with their use. In particular, aliphatic polyester polymers are known to have a relatively slow crystallization rate as compared to, for example, polyolefin polymers, thereby often resulting in poor processability of the aliphatic polyester polymers. Most aliphatic polyester polymers also have much lower melting temperatures than polyolefins and are difficult to cool sufficiently following thermal processing. Aliphatic polyester polymers are, in general, not inherently wettable materials and may need modifications for use in a personal care application. In addition, the use of processing additives may retard the biodegradation rate of the original material or the processing additives themselves may not be biodegradable.

Also, while degradable monocomponent fibers are known, problems have been encountered with their use. In particular, known degradable fibers typically do not have good thermal dimensional stability such that the fibers usually undergo severe heat-shrinkage due to the polymer chain relaxation during downstream heat treatment processes such as thermal bonding or lamination.

For example, although fibers prepared from poly(lactic acid)polymer are known, problems have been encountered with their use. In particular, poly(lactic acid) polymers are known to have a relatively slow crystallization rate as compared to, for example, polyolefin polymers, thereby often resulting in poor processability of the aliphatic polyester polymers. In addition, the poly(lactic acid) polymers generally do not have good thermal dimensional-stability. The poly(lactic acid) polymers usually undergo severe heat-shrinkage due to the relaxation of the polymer chain during downstream heat treatment processes, such as thermal bonding and lamination, unless an extra step such as heat setting is taken. However, such a heat setting step generally limits the use of the fiber in in-situ nonwoven forming processes, such as spunbond and meltblown, where heat setting is very difficult to be accomplished.

Additionally, one of the more important components of many personal care articles is the body-side liner. The liner is usually comprised of a surfactant-treated polyolefin spunbond. For a spunbond to be implemented as a liner, it is desired that the material be wettable to promote intake of fluid insults. In addition to rapid intake, it is desired that the composite absorbent product keep the user's skin dry. In addition, it is desirable for the spunbond material to feel soft against the skin. The current spunbond diaper liner has a number of problems associated with it. First, it is comprised of polyolefinic materials and does not degrade. Due to the hydrophobic nature of these materials, the liner must be treated with a surfactant to make it wttable. Because there is no permanent anchoring of the surfactant to the polyolefin, it has a tendency to wash off during multiple insults, increasing intake times of the nonwovens.

Accordingly, there is a need for a disposable article with improved fluid management properties such as faster intake times and improved skin dryness. Additionally there is a need for a disposable article that is biodegradable while also providing these improved fluid management properties.

SUMMARY OF THE INVENTION

It is therefore desired to provide a disposable article having improved fluid management properties.

It is also desired to provide a disposable article having faster intake times.

It is also desired to provide a disposable article having improved skin dryness.

It is also desired to provide a disposable article that is biodegradable while also providing improved fluid management properties.

It is also desired to provide a disposable article having a nonwoven material comprising a thermoplastic composition which exhibits desired processability, liquid wettability, and thermal dimensional-stability properties.

It is also desired to provide a disposable article having a nonwoven material comprising a thermoplastic composition which may be easily and efficiently formed into a fiber.

It is also desired to provide a disposable article having a nonwoven material comprising a thermoplastic composition which is suitable for use in preparing nonwoven structures.

It is also desired to provide a disposable absorbent product that may be used for the absorption of fluids such as bodily fluids, yet which such disposable absorbent product comprises components that are readily degradable in the environment.

These desires are fulfilled by the present invention which provides a disposable article having a nonwoven material comprising a thermoplastic composition that is substantially biodegradable and yet which is easily prepared and readily processable into desired final nonwoven structures.

One aspect of the present invention concerns a disposable article having a nonwoven material having a thermoplastic composition that comprises a mixture of a first component, a second component, and a third component.

One embodiment of such a thermoplastic composition comprises a mixture of an aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid, wherein the multicarboxylic acid has a total of carbon atoms that is less than about 30; and a wetting agent which exhibits a hydrophilic-lipophilic balance ratio that is between about 10 to about 40, wherein the thermoplastic composition exhibits desired properties.

In another aspect, the present invention concerns a multicomponent fiber that is substantially degradable and yet which is easily prepared and readily processable into the desired final nonwoven structures.

One aspect of the present invention concerns a multicomponent fiber that comprises an unreacted mixture of aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid, wherein the multicarboxylic acid has a total of carbon atoms that is less than about 30; and a wetting agent which exhibits a hydrophilic-lipophilic balance ratio that is between about 10 to about 40.

In another aspect, the present invention concerns a disposable article having a nonwoven structure comprising the multicomponent fiber disclosed herein.

One embodiment of such a nonwoven structure is a frontsheet useful in a disposable absorbent product.

In another aspect, the present invention concerns a disposable absorbent product comprising the multicomponent fiber disclosed herein.

DETAILED DESCRIPTION OF THE INVENTION

The present invention is directed to a disposable absorbent product having a biodisintegratable nonwoven material which includes a thermoplastic composition comprising a first component, a second component, and a third component. As used herein, the term "thermoplastic" is meant to refer to a material that softens when exposed to heat and substantially returns to its original condition when cooled to room temperature.

It has been discovered that, by using an unreacted mixture of the components described herein, a thermoplastic composition may be prepared wherein such thermoplastic composition is substantially degradable yet which thermoplastic composition is easily processed into fibers and nonwoven structures that exhibit effective fibrous mechanical properties.

The first component in the thermoplastic composition is an aliphatic polyester polymer selected from the group consisting of a polybutylene succinate polymer, a polybutylene succinate-co-adipate polymer, a polycaprolactone polymer, a mixture of such polymers, or a copolymer of such polymers.

A polybutylene succinate polymer is generally prepared by the condensation polymerization of a glycol and a dicarboxylic acid or an acid anhydride thereof. A polybutylene succinate polymer may either be a linear polymer or a long-chain branched polymer. A long-chain branched polybutylene succinate polymer is generally prepared by using an additional polyfunctional component selected from the group consisting of trifunctional or tetrafunctional polyols, oxycarboxylic acids, and polybasic carboxylic acids. Polybutylene succinate polymers are known in the art and are described, for example, in European Patent Application 0 569 153 A2 to Showa Highpolymer Co., Ltd., Tokyo, Japan.

A polybutylene succinate-co-adipate polymer is generally prepared by the polymerization of at least one alkyl glycol and more than one aliphatic multifunctional acid. Polybutylene succinate-co-adipate polymers are also known in the art.

Examples of polybutylene succinate polymers and polybutylene succinate-co-adipate polymers that are suitable for use in the present invention include a variety of polybutylene succinate polymers and polybutylene succinate-coadipate polymers that are available from Showa Highpolymer Co., Ltd., Tokyo, Japan, under the designation BIONOLLE™ 1020 polybutylene succinate polymer or BIONOLLE™ 3020 polybutylene succinate-co-adipate polymer, which are essentially linear polymers. These materials are known to be substantially biodegradable.

A polycaprolactone polymer is generally prepared by the polymerization of ε-caprolactone. Examples of polycaprolactone polymers that are suitable for use in the present invention include a variety of polycaprolactone polymers that are available from Union Carbide Corporation, Somerset, N.J., under the designation TONE™ Polymer P767E and TONE™ Polymer P787 polycaprolactone polymers. These materials are known to be substantially biodegradable.

It is generally desired that the aliphatic polyester polymer selected from the group consisting of a polybutylene succinate polymer, a polybutylene succinate-co-adipate polymer, a polycaprolactone polymer, a mixture of such polymers, or a copolymer of such polymers be present in the thermoplastic composition in an amount effective to result in the thermoplastic composition exhibiting desired properties. The aliphatic polyester polymer will be present in the thermoplastic composition in a weight amount that is greater than 0 but less than 100 weight percent, beneficially between about 40 weight percent to less than 100 weight percent, more beneficially between about 50 weight percent to about 95 weight percent, suitably between about 60 weight percent to about 90 weight percent, more suitably between about 60 weight percent to about 80 weight percent, and most suitably between about 70 weight percent to about 75 weight percent, wherein all weight percents are based on the total weight amount of the aliphatic polyester polymer, the multicarboxylic acid, and the wetting agent present in the thermoplastic composition.

It is generally desired that the aliphatic polyester polymer exhibit a weight average molecular weight that is effective for the thermoplastic composition to exhibit desirable melt strength, fiber mechanical strength, and fiber spinning properties. In general, if the weight average molecular weight of an aliphatic polyester polymer is too high, this represents that the polymer chains are heavily entangled which may result in a thermoplastic composition comprising that aliphatic polyester polymer being difficult to process. Conversely, if the weight average molecular weight of an aliphatic polyester polymer is too low, this represents that the polymer chains are not entangled enough which may result in a thermoplastic composition comprising that aliphatic polyester polymer exhibiting a relatively weak melt strength, making high speed processing very difficult. Thus, aliphatic polyester polymers suitable for use in the present invention exhibit weight average molecular weights that are beneficially between about 10,000 to about 2,000,000, more beneficially between about 50,000 to about 400,000, and suitably between about 100,000 to about 300,000. The weight average molecular weight for polymers or polymer blends can be determined by methods known to those skilled in the art.

It is also desired that the aliphatic polyester polymer exhibit a polydispersity index value that is effective for the thermoplastic composition to exhibit desirable melt strength, fiber mechanical strength, and fiber spinning properties. As used herein, "polydispersity index" is meant to represent the value obtained by dividing the weight average molecular weight of a polymer by the number average molecular weight of the polymer. The number average molecular weight for polymers or polymer blends can be determined by methods known to those skilled in the art. In general, if the polydispersity index value of an aliphatic polyester polymer is too high, a thermoplastic composition comprising that aliphatic polyester polymer may be difficult to process due to inconsistent processing properties caused by polymer segments comprising low molecular weight polymers that have lower melt strength properties during spinning. Thus, it is desired that the aliphatic polyester polymer exhibits a polydispersity index value that is beneficially between about 1 to about 15, more beneficially between about 1 to about 4, and suitably between about 1 to about 3.

It is generally desired that the aliphatic polyester polymer be melt processable. It is therefore desired that the aliphatic polyester polymer exhibit a melt flow rate that is beneficially between about 1 gram per 10 minutes to about 200 grams per 10 minutes, suitably between about 10 grams per 10 minutes to about 100 grams per 10 minutes, and more suitably between about 20 grams per 10 minutes to about 40 grams per 10 minutes. The melt flow rate of a material may be determined, for example, according to ASTM Test Method D1238-E, incorporated in its entirety herein by reference.

In the present invention, it is desired that the aliphatic polyester polymer be substantially biodegradable. As a result, the disposable absorbent product comprising the thermoplastic composition will be substantially degradable when disposed of to the environment and exposed to air and/or water. As used herein, "biodegradable" is meant to represent that a material degrades from the action of naturally occurring microorganisms such as bacteria, fungi, and algae. The biodegradability of a material may be determined using ASTM Test Method 5338.92 or ISO CD Test Method 14855, each incorporated in their entirety herein by reference. In one particular embodiment, the biodegradability of a material may be determined using a modified ASTM Test Method 5338.92, wherein the test chambers are maintained at a constant temperature of about 58° C. throughout the testing rather than using an incremental temperature profile.

In the present invention, it is also desired that the aliphatic polyester polymer be substantially compostable. As a result, the disposable absorbent product comprising the aliphatic polyester polymer will be substantially compostable when disposed of to the environment and exposed to air and/or water. As used herein, "compostable" is meant to represent that a material is capable of undergoing biological decomposition in a compost site such that the material is not visually distinguishable and breaks down into carbon dioxide, water, inorganic compounds, and biomass, at a rate consistent with known compostable materials.

The second component in the thermoplastic composition is a multicarboxylic acid. A multicarboxylic acid is any acid that comprises two or more carboxylic acid groups. In one embodiment of the present invention, it is preferred that the multicarboxylic acid be linear. Suitable for use in the present invention are dicarboxylic acids, which comprise two carboxylic acid groups. It is generally desired that the multicarboxylic acid have a total number of carbons that is not too large because then the crystallization kinetics, the speed at which crystallization occurs of a fiber or nonwoven structure prepared from a thermoplastic composition of the present invention, could be slower than is desired. It is therefore desired that the multicarboxylic acid have a total of carbon atoms that is beneficially less than about 30, more beneficially between about 4 to about 30, suitably between about 5 to about 20, and more suitably between about 6 to about 10. Suitable multicarboxylic acids include, but are not limited to, succinic acid, glutaric acid, adipic acid, pimelic acid, suberic acid, azelaic acid, sebacic acid, and mixtures of such acids.

It is generally desired that the multicarboxylic acid be present in the thermoplastic composition in an amount effective to result in the thermoplastic composition exhibiting desired properties. The multicarboxylic acid will be present in the thermoplastic composition in a weight amount that is greater than 0 weight percent, beneficially between greater than 0 weight percent to about 30 weight percent, more beneficially between about 1 weight percent to about 30 weight percent, suitably between about 5 weight percent to about 25 weight percent, more suitably between about 5 weight percent to about 20 weight percent, and most suitably between about 5 weight percent to about 15 weight percent, wherein all weight percents are based on the total weight amount of the aliphatic polyester polymer, the multicarboxylic acid, and the wetting agent present in the thermoplastic composition.

In order for a thermoplastic composition used in the present invention to be processed into a nonwoven material, and subsequently a disposable absorbent product, that exhibits the properties desired in the present invention, it has been discovered that it is generally desired that the multicarboxylic acid beneficially exists in a liquid state during thermal processing of the thermoplastic composition but that during cooling of the processed thermoplastic composition, the multicarboxylic acid turns into a solid state, or crystallizes, before the aliphatic polyester polymer turns into a solid state, or crystallizes.

In the thermoplastic composition, the multicarboxylic acid is believed to perform two important, but distinct, functions. First, when the thermoplastic composition is in a molten state, the multicarboxylic acid is believed to function as a process lubricant or plasticizer that facilitates the processing of the thermoplastic composition while increasing the flexibility and toughness of a nonwoven material through internal modification of the aliphatic polyester polymer. While not intending to be bound hereby, it is believed that the multicarboxylic acid replaces the secondary valence bonds holding together the aliphatic polyester polymer chains with multicarboxylic acid-to-aliphatic polyester polymer valence bonds, thus facilitating the movement of the polymer chain segments. With this effect, the torque needed to turn an extruder is generally dramatically reduced as compared with the processing of the aliphatic polyester polymer alone. In addition, the process temperature required to spin the thermoplastic composition into the nonwoven material is generally dramatically reduced, thereby decreasing the risk for thermal degradation of the aliphatic polyester polymer while also reducing the amount and rate of cooling needed for the nonwoven material prepared. Second, when the nonwoven material is being cooled and solidified from its liquid or molten state, the multicarboxylic acid is believed to function as a nucleating agent. Aliphatic polyester polymers are known to have a very slow crystallization rate. Traditionally, there are two major ways to resolve this issue. One is to change the cooling temperature profile in order to maximize the crystallization kinetics, while the other is to add a nucleating agent to increase the sites and degree of crystallization.

The process of cooling an extruded polymer to ambient temperature is usually achieved by blowing ambient or sub-ambient temperature air over the extruded polymer. Such a process can be referred to as quenching or super-cooling because the change in temperature is usually greater than 100° C. and most often greater than 150° C. over a relatively short time frame (seconds). By reducing the melt viscosity of a polymer, such polymer may generally be extruded successfully at lower temperatures. This will generally reduce the temperature change needed upon cooling, to preferably be less than 150° C. and, in some cases, less than 100° C. To customize this common process further into the ideal cooling temperature profile needed to be the sole method of maximizing the crystallization kinetics of aliphatic polyesters in a real manufacturing process is very difficult because of the extreme cooling needed within a very short period of time. Standard cooling methods can be used in combination with a second method of modification, though. The traditional second method is to have a nucleating agent, such as solid particulates, mixed with a thermoplastic composition to provide sites for initiating crystallization during quenching. However, such solid nucleating agents generally agglomerate very easily in the thermoplastic composition which can result in the blocking of filters and spinneret holes during spinning. In addition, the nucleating affect of such solid nucleating agents usually peaks at add-on levels of about 1 percent of such solid nucleating agents. Both of these factors generally reduce the ability or the desire to add in high weight percentages of such solid nucleating agents into the thermoplastic composition. In the processing of the thermoplastic composition, however, it has been found that the multicarboxylic acid generally exists in a liquid state during the extrusion process, wherein the multicarboxylic acid functions as a plasticizer, while the multicarboxylic acid is still able to solidify or crystallize before the aliphatic polyester during cooling, wherein the multicarboxylic acid functions as a nucleating agent. It is believed that upon cooling from the homogeneous melt, the multicarboxylic acid solidifies or crystallizes relatively more quickly and completely just as it falls below its melting point since it is a relatively small molecule. For example, adipic acid has a melting temperature of about 162° C. and a crystallization temperature of about 145° C.

The aliphatic polyester polymer, being a macromolecule, has a relatively very slow crystallization rate which means that when cooled it generally solidifies or crystallizes more slowly and at a temperature lower than its melting temperature. During such cooling, then, the multicarboxylic acid starts to crystallize before the aliphatic polyester polymer and generally acts as solid nucleating sites within the cooling thermoplastic composition.

Another major difficulty encountered in the thermal processing of aliphatic polyester polymers into nonwoven materials and disposable absorbent products is the sticky nature of these polymers. Attempts to draw the fibers, either mechanically, or through an air drawing process, will often result in the aggregation of the fibers into a solid mass. It is generally known that the addition of a solid filler will in most cases act to reduce the tackiness of a polymer melt. However, the use of a solid filler can be problematic in a nonwoven application were a polymer is extruded through a hole with a very small diameter. This is because the filler particles tend to clog spinneret holes and filter screens, thereby interrupting the fiber spinning process. In the present invention, in contrast, the multicarboxylic acid generally remains a liquid during the extrusion process, but then solidifies almost immediately during the quench process. Thus, the multicarboxylic acid effectively acts as a solid filler, enhancing the overall crystallinity of the system and reducing the tackiness of the fibers and eliminating problems such as fiber aggregation during drawing.

It is desired that the multicarboxylic acid have a high level of chemical compatibility with the aliphatic polyester polymer that the multicarboxylic acid is being mixed with. While the prior art generally demonstrates the feasibility of a polylactide-adipic acid mixture, a unique feature was discovered in this invention. A polylactide-adipic acid mixture can generally only be blended with a relatively minor amount of a wetting agent, such as less than about two weight percent of a wetting agent, and, even then, only with extreme difficulty. Polybutylene succinate, polybutylene succinate-co-adipate, and polycaprolactone have been found to be very compatible with large quantities of both a multicarboxylic acid and a wetting agent. The reason for this is believed to be due to the chemical structure of the aliphatic polyester polymers. Polylactide polymer has a relatively bulky chemical structure, with no linear portions that are longer than $CH_2$. In other words, each $CH_2$ segment is connected to carbons bearing either an oxygen or other side chain. Thus, a multicarboxylic acid, such as adipic acid, can not align itself close to the polylactide polymer backbone. In the case of polybutylene succinate and polybutylene succinate-co-adipate, the polymer backbone has the repeating units $(CH_2)_2$ and $(CH_2)_4$ within its structure. Polycaprolactone has the repeating unit $(CH_2)_5$. These relatively long, open, linear portions that are unhindered by oxygen atoms and bulky side chains align well with a suitable multicarboxylic acid, such as adipic acid, which also has a $(CH_2)_4$ unit, thereby allowing very close contact between the multicarboxylic acid and the suitable aliphatic polyester polymer molecules. This excellent compatibility between the multicarboxylic acid and the aliphatic polyester polymer in these special cases has been found to relatively easily allow for the incorporation of a wetting agent, the third component in the present invention. Such suitable compatibility is evidenced by the ease of compounding and fiber or nonwoven production of mixtures containing polybutylene succinate, polybutylene succinate-co-adipate, polycaprolactone, or a blend or copolymer of these polymers with suitable multicarboxylic acids and wetting agents. The processability of these mixtures is excellent, while in the case of a polylactide-multicarboxylic acid system, a wetting agent can generally not be easily incorporated into the mixture.

Either separately or when mixed together, a polybutylene succinate polymer, a polybutylene succinate-co-adipate polymer, a polycaprolactone polymer, a mixture of such polymers, or a copolymer of such polymers are generally hydrophobic. Since it is desired that the nonwoven materials and disposable absorbent products prepared from the thermoplastic composition generally be hydrophilic, it has been found that there is a need for the use of another component in the thermoplastic composition to achieve the desired properties. As such, the thermoplastic composition preferably includes a wetting agent.

Thus, the third component in the thermoplastic composition is a wetting agent for the polybutylene succinate polymer, polybutylene succinate-co-adipate polymer, polycaprolactone polymer, a mixture of such polymers, and/or a copolymer of such polymers. Wetting agents suitable for use in the present invention will generally comprise a hydrophilic section which will generally be compatible with the hydrophilic sections of polybutylene succinate polymer, a polybutylene succinate-co-adipate polymer, a polycaprolactone polymer, a mixture of such polymers, or a copolymer of such polymers and a hydrophobic section which will generally be compatible with the hydrophobic sections of polybutylene succinate polymer, a polybutylene succinate-co-adipate polymer, a polycaprolactone polymer, a mixture of such polymers, or a copolymer of such polymers. These hydrophilic and hydrophobic sections of the wetting agent will generally exist in separate blocks so that the overall wetting agent structure may be di-block or random block. A wetting agent with a melting temperature below, or only slightly above, that of the aliphatic polyester polymer is preferred so that during the quenching process the wetting agent remains liquid after the aliphatic polyester polymer has crystallized. This will generally cause the wetting agent to migrate to the surface of the prepared fibrous structure, thereby improving wetting characteristics and improving processing of the fibrous structure. It is then generally desired that the wetting agent serves as a surfactant in a disposable absorbent product processed from the thermoplastic composition by modifying the contact angle of water in air of the processed material. The hydrophobic portion of the wetting agent may be, but is not limited to, a polyolefin such as polyethylene or polypropylene. The hydrophilic portion of the wetting agent may contain ethylene oxide, ethoxylates, glycols, alcohols or any combinations thereof. Examples of suitable wetting agents include UNITHOX®480 and UNITHOX®750 ethoxylated alcohols, or UNICID™ acid amide ethoxylates, all available from Petrolite Corporation of Tulsa, Okla.

Other suitable surfactants can, for example, include one or more of the following:

a. surfactants composed of silicone glycol copolymers, such as D193 and D1315 silicone glycol copolymers, which are available from Dow Corning Corporation, located in Midland, Mich.

b. ethoxylated alcohols such as GENAPOL™ 24-L-60, GENAPOL™ 24-L-92, or GENAPOL™ 24-L-98N ethoxylated alcohols, which may be obtained from Hoechst Celanese Corp., of Charlotte, N.C.

c. surfactants composed of ethoxylated mono- and diglycerides, such as MAZOL™ 80 MGK ethoxylated diglycerides, which is available from PPG Industries, Inc., of Gurnee, Ill.

d. surfactants composed of carboxylated alcohol ethoxylates, such as SANDOPAN™ DTC, SANDOPAN™ KST, or SANDOPAN™ DTC-100 carboxylated alcohol ethoxylates, which may be obtained from Sandoz Chemical Corp.

e. ethoxylated fatty esters such as TRYLON™ 5906 and TRYLON™ 5909 ethoxylated fatty esters, which may be obtained from Henkel Corp./Emery Grp. of Cincinnati, Ohio.

It is generally desired that the wetting agent exhibit a weight average molecular weight that is effective for the thermoplastic composition to exhibit desirable melt strength, fiber mechanical strength, and fiber spinning properties. In general, if the weight average molecular weight of a wetting agent is too high, the wetting agent will not blend well with the other components in the thermoplastic composition because the wetting agent's viscosity will be so high that it lacks the mobility needed to blend. Conversely, if the weight average molecular weight of the wetting agent is too low, this represents that the wetting agent will generally not blend well with the other components and have such a low viscosity that it causes processing problems. Thus, wetting agents suitable for use in the present invention exhibit weight average molecular weights that are beneficially between about 1,000 to about 100,000, suitably between about 1,000 to about 50,000, and more suitably between about 1,000 to about 10,000. The weight average molecular weight of a wetting agent may be determined using methods known to those skilled in the art.

It is generally desired that the wetting agent exhibit an effective hydrophilic-lipophilic balance ratio (HLB ratio). The HLB ratio of a material describes the relative ratio of the hydrophilicity of the material. The HLB ratio is calculated as the weight average molecular weight of the hydrophilic portion divided by the total weight average molecular weight of the material, which value is then multiplied by 20. If the HLB ratio value is too low, the wetting agent will generally not provide the desired improvement in hydrophilicity. Conversely, if the HLB ratio value is too high, the wetting agent will generally not blend into the thermoplastic composition because of chemical incompatibility and differences in viscosities with the other components. Thus, wetting agents useful in the present invention exhibit HLB ratio values that are beneficially between about 10 to about 40, suitably between about 10 to about 20, and more suitably between about 12 to about 16. The HLB ratio value for a particular wetting agent is generally well known and/or may be obtained from a variety of known technical references.

It is generally desired that the hydrophobic portion of the wetting agent be a linear hydrocarbon chain containing $(CH_2)_n$, where n is preferred to be 4 or greater. This linear hydrocarbon, hydrophobic part is generally highly compatible with similar sections in the polybutylene succinate, polybutylene succinate-co-adipate, and polycaprolactone polymers, as well as many multicarboxylic acids, such as adipic acid. By taking advantage of these structural similarities, the hydrophobic portions of the wetting agent will very closely bind to the aliphatic polyester polymer, while the hydrophilic portions will be allowed to extend out to the surface of a prepared nonwoven material. The general consequence of this phenomenon is a relatively large reduction in the advancing contact angle exhibited by the prepared nonwoven material. Examples of suitable wetting agents include UNITHOX®480 and UNITHOX®750 ethoxylated alcohols, available from Petrolite Corporation of Tulsa, Okla. These wetting agents have an average linear hydrocarbon chain length between 26 and 50 carbons. If the hydrophobic portion of the wetting agent is too bulky, such as with phenyl rings or bulky side chains, such a wetting agent will generally not be well incorporated into the aliphatic polyester polymer blend. Rather than having the hydrophobic portions of the wetting agent being bound to the aliphatic polyester polymer molecules, with the hydrophilic portions of the wetting agent hanging free, entire molecules of the wetting agent molecules will float freely in the mixture, becoming entrapped in the blend. This is evidenced by a high advancing contact angle and a relatively low receding contact angle, indicating that the hydrophilic chains are not on the surface. After a liquid insult, the wetting agent can migrate to the surface resulting in a low receding contact angle. This is clearly demonstrated through the use of IGEPAL™ RC-630 ethoxylated alkyl phenol surfactant, obtained from Rhone-Poulenc, located in Cranbury, N.J. IGEPAL™ RC-630 ethoxylated alkyl phenol has a bulky phenyl group which limits its compatibility with aliphatic polyester polymers, as evidenced by the high advancing contact angle and low receding contact angle of a mixture of an aliphatic polyester polymer and the IGEPAL™ RC-630 ethoxylated alkyl phenol.

It is generally desired that the wetting agent be present in the thermoplastic composition in an amount effective to result in the thermoplastic composition exhibiting desired properties such as desirable contact angle values. In general, too much of the wetting agent may lead to processing problems of the thermoplastic composition or to a final thermoplastic composition that does not exhibit desired properties such as desired advancing and receding contact angle values. The wetting agent will beneficially be present in the thermoplastic composition in a weight amount that is greater than 0 to about 25 weight percent, more beneficially between about 0.5 weight percent to about 20 weight percent, suitably between about 1 weight percent to about 20 weight percent, and more suitably between about 1 weight percent to about 15 weight percent, wherein all weight percents are based on the total weight amount of the polybutylene succinate polymer, a polybutylene succinate-co-adipate polymer, a polycaprolactone polymer, a mixture of such polymers, or a copolymer of such polymers; the multicarboxylic acid, and the wetting agent present in the thermoplastic composition.

While the principal components of the thermoplastic composition used in the present invention have been described in the foregoing, such thermoplastic composition is not limited thereto and can include other components not adversely effecting the desired properties of the thermoplastic composition. Exemplary materials which could be used as additional components would include, without limitation, pigments, antioxidants, stabilizers, surfactants, waxes, flow promoters, solid solvents, plasticizers, nucleating agents, particulates, and other materials added to enhance the processability of the thermoplastic composition. If such additional components are included in a thermoplastic composition, it is generally desired that such additional components be used in an amount that is beneficially less than about 10 weight percent, more beneficially less than about 5 weight percent, and suitably less than about 1 weight percent, wherein all weight percents are based on the total weight amount of the aliphatic polyester polymer selected from the group consisting of a polybutylene succinate polymer, a polybutylene succinate-co-adipate polymer, a polycaprolactone polymer, a mixture of such polymers, or a copolymer of such polymers; a multicarboxylic acid; and a wetting agent present in the thermoplastic composition.

The thermoplastic composition used in the present invention is generally the resulting morphology of a mixture of the aliphatic polyester polymer, the multicarboxylic acid, the wetting agent and, optionally, any additional components. In order to achieve the desired properties for the thermoplastic composition of the present invention, it has been discovered that it is critical that the aliphatic polyester polymer, the multicarboxylic acid, and the wetting agent remain substantially unreacted with each other such that a copolymer comprising each of the aliphatic polyester polymer, the multicarboxylic acid, and/or the wetting agent is not formed. As such, each of the aliphatic polyester polymer, the multicarboxylic acid, and the wetting agent remain distinct components of the thermoplastic composition.

Each of the aliphatic polyester polymer, the multicarboxylic acid, and the wetting agent will generally form separate regions or domains within a prepared mixture forming the thermoplastic composition. However, depending on the relative amounts that are used of each of the aliphatic polyester polymer, the multicarboxylic acid, and the wetting agent, an essentially continuous phase may be formed from the polymer that is present in the thermoplastic composition in a relatively greater amount.

In one embodiment of a thermoplastic composition or a multicomponent fiber used in the present invention, after dry mixing together the aliphatic polyester polymer, the multicarboxylic acid, and the wetting agent to form a thermoplastic composition dry mixture, such thermoplastic composition dry mixture is beneficially agitated, stirred, or otherwise blended to effectively uniformly mix the aliphatic polyester polymer, the multicarboxylic acid, and the wetting agent such that an essentially homogeneous dry mixture is formed. The dry mixture may then be melt blended in, for example, an extruder, to effectively uniformly mix the aliphatic polyester polymer, the multicarboxylic acid, and the wetting agent such that an essentially homogeneous melted mixture is formed. The essentially homogeneous melted mixture may then be cooled and pelletized. Alternatively, the essentially homogeneous melted mixture may be sent directly to a spin pack or other equipment for forming a nonwoven material used in the disposable absorbent product.

Alternative methods of mixing together the components of the present invention include adding the multicarboxylic acid and the wetting agent to the aliphatic polyester polymer in, for example, an extruder being used to mix the components together. In addition, it is also possible to initially melt mix all of the components together at the same time. Other methods of mixing together the components of the present invention are also possible and will be easily recognized by one skilled in the art. In order to determine if the aliphatic polyester polymer, the multicarboxylic acid, and the wetting agent remain essentially unreacted, it is possible to use techniques, such as nuclear magnetic resonance and infrared analysis, to evaluate the chemical characteristics of the final thermoplastic composition.

Typical conditions for thermally processing the various components include using a shear rate that is beneficially between about 100 seconds$^{-1}$ to about 50000 seconds$^{-1}$, more beneficially between about 500 seconds$^{-1}$ to about 5000 seconds$^{-1}$, suitably between about 1000 seconds$^{-1}$ to about 3000 seconds$^{-1}$, and most suitably at about 1000 seconds$^{-1}$. Typical conditions for thermally processing the components also include using a temperature that is beneficially between about 50° C. to about 500° C., more beneficially between about 75° C. to about 300° C., and suitably between about 100° C. to about 250° C.

As used herein, the term "hydrophobic" refers to a material having a contact angle of water in air of at least 90 degrees. In contrast, as used herein, the term "hydrophilic" refers to a material having a contact angle of water in air of less than 90 degrees. However, commercial personal care products generally require contact angles that are significantly below 90 degrees in order to provide desired liquid transport properties. In order to achieve the rapid intake and wetting properties desired for personal care products, the contact angle of water in air is generally desired to fall below about 70 degrees. In general, the lower the contact angle, the better the wettability. For the purposes of this application, contact angle measurements are determined as set forth in the Test Methods section herein. The general subject of contact angles and the measurement thereof is well known in the art as, for example, in Robert J. Good and Robert J. Stromberg, Ed., in "Surface and Colloid Science—Experimental Methods", Vol. 11, (Plenum Press, 1979).

The resultant disposable absorbent products of the present invention are desired to exhibit an improvement in hydrophilicity, evidenced by a decrease in the contact angle of water in air. The contact angle of water in air of a fiber sample can be measured as either an advancing or a receding contact angle value because of the nature of the testing procedure. The advancing contact angle measures a material's initial response to a liquid, such as water. The receding contact angle gives a measure of how a material will perform over the duration of a first insult, or exposure to liquid, as well as over following insults. A lower receding contact angle means that the material is becoming more hydrophilic during the liquid exposure and will generally then be able to transport liquids more consistently. Both the advancing and receding contact angle data is desirably used to establish the highly hydrophilic nature of a multicomponent fiber or nonwoven structure used in the present invention.

The resultant nonwoven materials used in the present invention are desired to exhibit an improvement in the rate of liquid transport, as evidenced by a low contact angle hysteresis. As used herein, the contact angle hysteresis is defined as the difference between the advancing and receding contact angles for a material being evaluated. For example, a relatively high advancing contact angle and relatively low receding contact angle would lead to a large contact angle hysteresis. In such a case, an initial liquid insult would generally be slowly absorbed by a material, though the material would generally retain the liquid once absorbed. In general, relatively low advancing and receding contact angles, as well as a small contact angle hysteresis, are desired in order to have a high rate of liquid transport. Contact angle hysteresis may be used as an indication of the rate of wicking of a liquid on the material being evaluated.

In one embodiment of the present invention, it is desired that a multicomponent fiber or nonwoven material prepared from the thermoplastic composition described herein exhibits an Advancing Contact Angle value that is beneficially less than about 70 degrees, more beneficially less than about 65 degrees, suitably less than about 60 degrees, more suitably less than about 55 degrees, and most suitably less than about 50 degrees, wherein the Advancing Contact Angle value is determined by the method that is described in the Test Methods section herein.

In another embodiment of the present invention, it is desired that a multicomponent fiber or nonwoven material prepared from the thermoplastic composition described herein exhibits a Receding Contact Angle value that is beneficially less than about 60 degrees, more beneficially less than about 55 degrees, suitably less than about 50 degrees, more suitably less than about 45 degrees, and most suitably less than about 40 degrees, wherein the Receding Contact Angle value is determined by the method that is described in the Test Methods section herein.

In another embodiment of the present invention, it is desired that a multicomponent fiber or nonwoven material prepared from the thermoplastic composition described herein exhibits a Advancing Contact Angle value that is beneficially at least about 10 degrees, more beneficially at least about 15 degrees, suitably at least about 20 degrees, and more suitably at least about 25 degrees, less than the Advancing Contact Angle value that is exhibited by an otherwise substantially identical fiber or nonwoven structure prepared from a thermoplastic composition that does not comprise a wetting agent.

In another embodiment of the present invention, it is desired that a multicomponent fiber or nonwoven material prepared from the thermoplastic composition described herein exhibits a Receding Contact Angle value that is beneficially at least about 5 degrees, more beneficially at least about 10 degrees, suitably at least about 15 degrees, and more suitably at least about 20 degrees, less than the Receding Contact Angle value that is exhibited by an otherwise substantially identical fiber or nonwoven structure prepared from a thermoplastic composition that does not comprise a wetting agent.

As used herein, the term "otherwise substantially identical nonwoven material prepared from a thermoplastic composition that does not comprise a wetting agent", and other similar terms, is intended to refer to a control nonwoven material that is prepared using substantially identical materials and a substantially identical process as compared to a nonwoven material of the present invention, except that the control nonwoven material does not comprise or is not prepared with the wetting agent described herein.

In another embodiment of the present invention, it is desired that the difference between the Advancing Contact Angle value and the Receding Contact Angle value, referred to herein as the Contact Angle Hysteresis, be as small as possible. As such, it is desired that the multicomponent fiber exhibits a difference between the Advancing Contact Angle value and the Receding Contact Angle value that is beneficially less than about 50 degrees, more beneficially less than about 40 degrees, suitably less than about 30 degrees, and more suitably less than about 20 degrees.

It is generally desired that the melting or softening temperature of the thermoplastic composition be within a range that is typically encountered in most process applications. As such, it is generally desired that the melting or softening temperature of the thermoplastic composition beneficially be between about 25° C. to about 350° C., more beneficially be between about 35° C. to about 300° C., and suitably be between about 45° C. to about 250° C.

The thermoplastic composition used in the present invention has been found to generally exhibit improved processability properties as compared to a thermoplastic composition comprising the aliphatic polyester polymer but none of the multicarboxylic acid and/or the wetting agent. This is generally due to the significant reduction in viscosity that occurs due to the multicarboxylic acid and the internal lubricating effect of the wetting agent. Without the multicarboxylic acid, the viscosity of a mixture of the aliphatic polyester polymer and the wetting agent is generally too high to process. Without the wetting agent, a mixture of the aliphatic polyester polymer and the multicarboxylic acid is generally not a sufficiently hydrophilic material and generally does not have the processing advantages of the liquid wetting agent in the quench zone. It has been discovered as part of the present invention that only with the correct combination of the three components can the appropriate viscosity and melt strength be achieved for fiber spinning.

As used herein, the improved processability of a thermoplastic composition is measured as a decline in the apparent viscosity of the thermoplastic composition at a temperature of about 170° C. and a shear rate of about 1000 seconds$^{-1}$, typical industrial extrusion processing conditions. If the thermoplastic composition exhibits an apparent viscosity that is too high, the thermoplastic composition will generally be very difficult to process. In contrast, if the thermoplastic composition exhibits an apparent viscosity that is too low, the thermoplastic composition will generally result in an extruded fiber that has very poor tensile strength.

Therefore, it is generally desired that the thermoplastic composition exhibits an Apparent Viscosity value at a temperature of about 170° C. and a shear rate of about 1000 seconds$^{-1}$ that is beneficially between about 5 Pascal seconds (Pa.s) to about 200 Pascal seconds, more beneficially between about 10 Pascal seconds to about 150 Pascal seconds, and suitably between about 20 Pascal seconds to about 100 Pascal seconds. The method by which the Apparent Viscosity value is determined is set forth below in connection with the examples.

As used herein, the term "fiber" or "fibrous" is meant to refer to a material wherein the length to diameter ratio of such material is greater than about 10. Conversely, a "nonfiber" or "nonfibrous" material is meant to refer to a material wherein the length to diameter ratio of such material is about 10 or less.

Methods for making fibers are well known and need not be described here in detail. The melt spinning of polymers includes the production of continuous filament, such as spunbond or meltblown, and non-continuous filament, such as staple and short-cut fibers, structures. To form a spunbond or meltblown fiber, generally, a thermoplastic composition is extruded and fed to a distribution system where the thermoplastic composition is introduced into a spinneret plate. The spun fiber is then cooled, solidified, drawn by an aerodynamic system and then formed into a conventional nonwoven. Meanwhile, to produce short-cut or staple the spun fiber is cooled, solidified, and drawn, generally by a mechanical rolls system, to an intermediate filament diameter and collected fiber, rather than being directly formed into a nonwoven structure. Subsequently, the collected fiber may be "cold drawn" at a temperature below its softening temperature, to the desired finished fiber diameter and can be followed by crimping/texturizing and cutting to a desirable fiber length. Multicomponent fibers can be cut into relatively short lengths, such as staple fibers which generally have lengths in the range of about 25 to about 50 millimeters and short-cut fibers which are even shorter and generally have lengths less than about 18 millimeters. See, for example, U.S. Pat. No. 4,789,592 to Taniguchi et al, and U.S. Pat. No. 5,336,552 to Strack et al., both of which are incorporated herein by reference in their entirety.

The biodisintegratable nonwoven materials used in the present invention are suited for use in disposable products including disposable absorbent products such as diapers, adult incontinent products, and bed pads; in catamenial devices such as sanitary napkins, and tampons; and other absorbent products such as wipes, bibs, wound dressings, and surgical capes or drapes. Accordingly, in another aspect, the present invention relates to a disposable absorbent product comprising the multicomponent fibers.

In one embodiment of the present invention, the thermoplastic composition is formed into a fibrous matrix for incorporation into a disposable absorbent product. A fibrous matrix may take the form of, for example, a fibrous nonwoven web. Fibrous nonwoven webs may be made completely from fibers prepared from the thermoplastic composition of the present invention or they may be blended with other fibers. The length of the fibers used may depend on the particular end use contemplated. Where the fibers are to be degraded in water as, for example, in a toilet, it is advantageous if the lengths are maintained at or below about 15 millimeters.

In one embodiment of the present invention, a disposable absorbent product is provided, which disposable absorbent product generally comprises a composite structure including a liquid-permeable topsheet, a fluid acquisition layer, an absorbent structure, and a liquid-impermeable backsheet, wherein at least one of the liquid-permeable topsheet, the fluid acquisition layer, or the liquid-impermeable backsheet comprises the nonwoven material of the present invention. In some instances, it may be beneficial for all three of the topsheet, the fluid acquisition layer, and the backsheet to comprise the nonwoven material of the present invention.

In another embodiment, the disposable absorbent product may comprise generally a composite structure including a liquid-permeable topsheet, an absorbent structure, and a liquid-impermeable backsheet, wherein at least one of the liquid-permeable topsheet or the liquid-impermeable backsheet comprises the nonwoven material of the present invention.

In another embodiment of the present invention, the nonwoven material may be prepared on a spunbond line. Resin pellets comprising the thermoplastic materials previously described are formed and predried. Then, they are fed to a single extruder. The fibers may be drawn through a fiber draw unit (FDU) or air-drawing unit onto a forming wire and thermally bonded. However, other methods and preparation techniques may also be used.

Exemplary disposable absorbent products are generally described in U.S. Pat. Nos. 4,710,187; 4,762,521; 4,770,656; and 4,798,603; which references are incorporated herein by reference.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

TEST METHODS

Melting Temperature

The melting temperature of a material was determined using differential scanning calorimetry. A differential scanning calorimeter, under the designation Thermal Analyst 2910 Differential Scanning Calorimeter, which was outfitted with a liquid nitrogen cooling accessory and used in combination with Thermal Analyst 2200 analysis software (version 8.10) program, both available from T.A. Instruments Inc. of New Castle, Del., was used for the determination of melting temperatures.

The material samples tested were either in the form of fibers or resin pellets. It was preferred to not handle the material samples directly, but rather to use tweezers and other tools, so as not to introduce anything that would produce erroneous results. The material samples were cut, in the case of fibers, or placed, in the case of resin pellets, into an aluminum pan and weighed to an accuracy of 0.01 mg on an analytical balance. If needed, a lid was crimped over the material sample onto the pan.

The differential scanning calorimeter was calibrated using an indium metal standard and a baseline correction performed, as described in the manual for the differential scanning calorimeter. A material sample was placed into the test chamber of the differential scanning calorimeter for testing and an empty pan is used as a reference. All testing was run with a 55 cubic centimeter/minute nitrogen (industrial grade) purge on the test chamber. The heating and cooling program was a 2 cycle test that begins with equilibration of the chamber to −40° C., followed by a heating cycle of 20° C./minute to 200° C., followed by a cooling cycle at 20° C./minute to −40° C., and then another heating cycle of 20° C./minute to 200° C.

The results were evaluated using the analysis software program wherein the glass transition temperature (Tg) of inflection, endothermic and exothermic peaks were identified and quantified. The glass transition temperature was identified as the area on the line where a distinct change in slope occurs and then the melting temperature is determined using an automatic inflection calculation.

Apparent Viscosity

A capillary rheometer, under the designation Göttfert Rheograph 2003 capillary rheometer, which was used in combination with WinRHEO (version 2.31) analysis software, both available from Göttfert Company of Rock Hill, S.C., was used to evaluate the apparent viscosity rheological properties of material samples. The capillary rheometer setup included a 2000 bar pressure transducer and a 30 mm length/30 mm active length/1 mm diameter/0 mm height/180° run in angle, round hole capillary die.

If the material sample being tested demonstrated or was known to have water sensitivity, the material sample was dried in a vacuum oven above its glass transition temperature, i.e. above 55 or 60° C. for poly(lactic acid) materials, under a vacuum of at least 15 inches of mercury with a nitrogen gas purge of at least 30 standard cubic feet per hour for at least 16 hours.

Once the instrument was warmed up and the pressure transducer was calibrated, the material sample was loaded incrementally into the column, packing resin into the column with a ramrod each time to ensure a consistent melt during testing. After material sample loading, a 2 minute melt time preceded each test to allow the material sample to completely melt at the test temperature. The capillary rheometer took data points automatically and determined the apparent viscosity (in Pascal.second) at 7 apparent shear rates (in seconds$^{-1}$): 50, 100, 200, 500, 1000, 2000, and 5000. When examining the resultant curve it was important that the curve be relatively smooth. If there were significant deviations from a general curve from one point to another, possibly due to air in the column, the test run was repeated to confirm the results.

The resultant rheology curve of apparent shear rate versus apparent viscosity gives an indication of how the material sample will run at that temperature in an extrusion process. The apparent viscosity values at a shear rate of at least 1000 second$^{-1}$ are of specific interest because these are the typical conditions found in commercial fiber spinning extruders.

Contact Angle

The equipment includes a DCA-322 Dynamic Contact Angle Analyzer and WinDCA (version 1.02) software, both available from ATI-CAHN Instruments, Inc., of Madison, Wis. Testing was done on the "A" loop with a balance stirrup attached. Calibrations should be done monthly on the motor and daily on the balance (100 mg mass used) as indicated in the manual.

Thermoplastic compositions were spun into fibers and the freefall sample (jetstretch of 0) was used for the determination of contact angle. Care should be taken throughout fiber preparation to minimize fiber exposure to handling to ensure that contamination is kept to a minimum. The fiber sample was attached to the wire hanger with scotch tape such that 2–3 cm of fiber extended beyond the end of the hanger. Then the fiber sample was cut with a razor so that approximately 1.5 cm was extending beyond the end of the hanger. An optical microscope was used to determine the average diameter (3 to 4 measurements) along the fiber.

The sample on the wire hanger was suspended from the balance stirrup on loop "A". The immersion liquid was distilled water and it was changed for each specimen. The specimen parameters were entered (i.e. fiber diameter) and the test started. The stage advanced at 151.75 microns/second until it detected the Zero Depth of Immersion when the fiber contacted the surface of the distilled water. From the Zero Depth of Immersion, the fiber advanced into the water for 1 cm, dwelled for approximately 0 seconds and then immediately receded 1 cm. The auto-analysis of the contact angle done by the software determined the advancing and receding contact angles of the fiber sample based on standard calculations identified in the manual. Contact angles of 0 or <0 indicate that the sample had become totally wettable. Five replicates for each sample were tested and a statistical analysis for mean, standard deviation, and coefficient of variation percent was calculated. As reported in the examples herein and as used throughout the claims, the Advancing Contact Angle value represents the advancing contact angle of distilled water on a fiber sample determined according to the preceding test method. Similarly, as reported in the examples herein and as used throughout the claims, the Receding Contact Angle value represents the receding contact angle of distilled water on a fiber sample determined according to the preceding test method.

Nonwoven Tensile Testing

Tensile properties of the nonwoven webs were measured on a Sintech 1/D Model, obtained from MTS Systems Corporation, a company located in Eden Prairie Minn., using the Testworks 3.03 analysis software, also obtained from MTS Systems Corporation. A set of 10N pneumatic tensile grips was obtained from MTS (MTS model number 00.01659) and covered with rubber grip facings (MTS model number 38.00401). A 50 lb (about 200 N) load cell was used for this test method, and the rubber-faced, air-actuated grips, were attached to the machine. The power to both the load cell and the load frame was turned on and the equipment given a minimum of one half hour to warm up and stabilize. After this time had elapsed the test grips were moved manually until there is a 3 inch (7.62 cm) separation between the upper and lower grips, as measured with a ruler and a level. The distance was then zeroed on the test software. The grips were opened and the load cell was calibrated.

Samples were cut into one inch (2.54 cm) wide strips which were placed vertically in the grips so that there was no tension on the sample. The test was initiated by the software and the upper grip rose at a rate of 12.0 inches per minute (30.48 cm per minute), while the lower grip remained stationary. The test continued until the nonwoven failed, following which the upper grip returned to its starting point. The software then displayed the measured and calculated properties of the sample. The information of specific interest is MD % in elongation at the peak load. Peak load is the maximum load at any point during the test and is measured in grams.

Cup Crush Testing

Cup crush testing was performed on a Sintech 1/D model, obtained from MTS Systems Corporation, a company located in Eden Prairie Minn., using the Testworks 3.03 analysis software, also obtained from MTS Systems Corporation. In this method a 10 lb (about 50 N) load cell was attached to the frame of the Sintech. A forming cylinder was placed on the bottom attachment and a six inch (15.24 cm) by six inch (15.24 cm) nonwoven square was placed over the mouth of the cylinder. The forming cup was placed over the nonwoven, forming the nonwoven over the cylinder, leaving an open circle of the web exposed on top of the cylinder. The foot of the cup crush device consisted of a metal rod with a rounded end and was attached to the 10 lb. load cell. When the test was initiated, the foot descended at a rate of 409.40 mm per minute into the nonwoven web, crushing it. The Sintech then measured the peak load and energy required to crush the nonwoven. The foot descended a total distance of 62 mm and then stopped, reversed direction, and returned to its original position. In general a lower peak load indicates a softer nonwoven.

Fluid-intake and Flowback Evaluation (FIFE)

Fluid-Intake and Flowback Evaluation (FIFE) testing was used to determine the absorbency time and flowback of a personal care product. A Master-Flex Digi-Staltic Automatic Dispensing system was supplied with saline colored with a small amount of FD&C blue dye, set to provide 80 mL insults, and dispensed several times to eliminate any air bubbles. The product samples, infant care diapers, were prepared without elastics so that they would easily lie flat. Two 3.5 inch by 12 inch blotter paper samples were weighed. These papers were placed on the FIFE board, a simple board with a 3 inch by 6 inch raised platform in the middle. The blotter papers were aligned so that they ran lengthwise along either side of the raised platform. The diaper was then aligned so that the area to be insulted was carefully centered on the raised platform, with the topsheet facing up, such that there were no visible wrinkles in the nonwoven topsheet. The second FIFE board was then placed on top of the product. This apparatus consists of a flat board that was intersected by a hollow cylinder, protruding only from the top side of the board. The circular region created where the cylinder intersected the flat plane of the board was hollow. The inner diameter of the cylinder was 5.1 centimeters. A funnel with an inner diameter of 7 millimeters at the short end was placed in the cylinder. The fluid was then dispensed by the pump directly into the funnel. The intake time was recorded by stopwatch from the time the fluid hit the funnel to the moment no fluid was visible on the specimen surface. The blotter papers were checked for product leakage and if any occurred the weight of the blotter papers would have been measured to determine the quantity of fluid that leaked. In the described testing, no leakage occurred. Approximately one minute elapsed before the second insult was applied in the same manner. Again a third insult was applied and timed in the same manner. If desired a procedure may then follow to determine the amount of fluid flowing back when the product is under pressure. In this case, only the intake rates were recorded.

TransEpidermal Water Loss (TEWL)

TransEpidermal Water Loss (TEWL) armband testing was used to measure changes in skin hydration as a result of product use. A lower evaporation value, as measured by a Servo Med Evaporimeter, is indicative of a product that promotes skindryness. This test actually reports a difference in evaporation values. A measurement of moisture evaporation rate is taken prior to the test and then immediately following. The difference in these numbers provides the TEWL value as reported in the results. A lower TEWL value implies that a product provides better breathability to the skin.

Product, in this case infant care diapers, was prepared by hand without any elastics or ears. The basic structure of the diaper was the same, but one control diaper consisted entirely of standard materials and the other had all standard materials except for the topsheet, which was comprised of the biodisintegratable nonwoven. The target area for the insults was drawn in permanent marker on the outside of the product. All testing occurred in a controlled environment of 72±4° F. with a relative humidity of 40±5%. The subjects were adult women who were carefully selected to insure that they had no conditions that might potentially alter the results of such a test.

Subjects relaxed in a controlled environment until a stable baseline reading of less than 10 $g^2$/m/hr is obtained with the Servo Med Evaporimeter. These measurements were performed on the inner forearm of the subjects. Masterflex Digi-Staltic batch/dispense pump was used with silicone tubing in the pump head, which was connected to neoprene tubing for dispensing, by barb fittings. The end of the neoprene dispensing tube was placed on the forearm of a subject and the product applied to the forearm with the target insult area directly on top of the tube opening. The product is secured with tape that was wrapped around the diaper and did not contact the skin. The diaper was then loaded with three insults of 60 mL of saline at 45 second intervals and the tube removed. The product was further secured with a stretchable net and the subject required to sit for one hour.

After 60 minutes of wear, the product was removed and the Evaporimeter was then used to obtain readings every second for two minutes in the same area on the forearm as the baseline readings were taken. The reported result is the difference between the one-hour and baseline readings.

EXAMPLES

Various materials were used as components to form thermoplastic compositions and multicomponent fibers in the following Examples. The designation and various properties of these materials are listed in Table 1.

A poly(lactic acid) (PLA) polymer was obtained from Chronopol Inc., Golden, Colo. under the designation HEPLON™ A10005 poly(lactic acid) polymer.

A polybutylene succinate polymer, available from Showa Highpolymer Co., Ltd., Tokyo, Japan, under the designation BIONOLLE™ 1020 polybutylene succinate, was obtained. In Table 2, BIONOLLE™ 1020 polybutylene succinate polymer is designated as PBS.

A polybutylene succinate-co-adipate, available from Showa Highpolymer Co., Ltd., Tokyo, Japan, under the designation BIONOLLE™ 3020 polybutylene succinate-co-adipate, was obtained.

A polycaprolactone polymer was obtained from Union Carbide Chemicals and Plastics Company, Inc. under the designation TONE™ Polymer P767E polycaprolactone polymer.

A material used as a wetting agent was obtained from Petrolite Corporation of Tulsa, Okla., under the designation UNITHOX™ 480 ethoxylated alcohol, which exhibited a number average molecular weight of about 2250, an ethoxylate percent of about 80 weight percent, a melting temperature of about 65° C., and an HLB value of about 16.

A material used as a wetting agent was obtained from Baker Petrolite Corporation of Tulsa, Okla., under the designation UNICID™ X-8198 acid amide ethoxylate, which demonstrated an HLB value of approximately 35 and a melting temperature of approximately 60° C.

A material used as a wetting agent was obtained from Rhone-Poulenc, located in Cranbury, N.J., under the designation IGEPAL™ RC-630 ethoxylated alkyl phenol surfactant, which demonstrated an HLB value of about 12.7 and a melting temperature of about 4° C.

TABLE 1

| Material Designation | L:D Ratio | Melting Temp. (° C.) | Weight Average Molecular Weight | Number Average Molecular Weight | Polydispersity Index | Residual Lactic Acid Monomer |
|---|---|---|---|---|---|---|
| HEPLON A10005 | 100:0 | 175 | 187,000 | 118,000 | 1.58 | <1% |
| TONE P767E | N/A | 64 | 60,000 | 43,000 | 1.40 | N/A |
| BIONOLLE 1020 | N/A | 95 | 40,000 to 1,000,000 | 20,000 to 300,000 | ~2 to ~3.3 | N/A |
| BIONOLLE 3020 | N/A | 114 | 40,000 to 1,000,000 | 20,000 to 300,000 | ~2 to ~3.3 | N/A |

Examples 1–3

Thermoplastic compositions were prepared by taking the various components dry mixing them, followed by melt blending them in a counter-rotating twin screw extruder to provide vigorous mixing of the components. The melt mixing involves partial or complete melting of the components combined with the shearing effect of rotating mixing screws. Such conditions are conducive to optimal blending and even dispersion of the components of the thermoplastic composition. Twin screw extruders such as a Haake Rheocord 90 twin screw extruder, available from Haake GmbH of Karlsautte, Germany, or a Brabender twin screw mixer (cat no 05-96-000) available from Brabender Instruments of South Hackensack, N.J., or other comparable twin screw extruders, are well suited to this task. This also includes co-rotating twin screw extruders such as the ZSK-30 extruder, available from Werner and Pfleiderer Corporation of Ramsey, N.J. Unless otherwise indicated, all samples were prepared on a Haake Rheocord 90 twin screw extruder. The melted composition is cooled following extrusion from the melt mixer on either a liquid cooled roll or surface and/or by forced air passed over the extrudate. The cooled composition is then subsequently pelletized for conversion to fibers.

The conversion of these resins into fibers and nonwovens was conducted on an in-house spinning line with a 0.75 inch (1.905 cm) diameter extruder. The extruder has a 24:1 L:D (length:diameter) ratio screw and three heating zones which feed into a transfer pipe from the extruder to the spin pack. The transfer pipe constitutes the 4th and 5th heating zones and contains a 0.62 inch diameter KOCH™ SMX type static mixer unit, available from Koch Engineering Company Inc. of New York, N.Y. The transfer pipe extends into the spinning head (6th heating zone) and through a spin plate with numerous small holes which the molten polymer is extruded through. The spin plate used herein had 15 holes, where each hole has a 20 mil (0.508 mm) diameter. The fibers are air quenched using air at a temperature of 13° C. to 22° C., drawn down by a mechanical draw roll, and passed on either to a winder unit for collection, or to a fiber drawing unit for spunbond formation and bonding. Alternatively other accessory equipment may be used for treatment before collection.

The polymers were converted to a spunbond nonwoven material and were performed using 14" and 20" fiber spinning lines. A monocomponent fiber was produced from a single extruder and the fibers were drawn and laid through a fiber draw unit (FDU). The webs were then thermally bonded inline with a wire-weave bond pattern.

The results for advancing and receding contact angles are given in Table 2. The Advancing Contact Angle is a measure of how a material will interact with fluid during its first contact with liquid. The Receding Contact Angle is an indication of how the material will behave during multiple insults with liquid or in a damp, high humidity environment. The blends included in this invention produced highly wettable fibers.

TABLE 2

Contact Angle Data

| Material | Advancing Contact Angle | Receding Contact Angle |
|---|---|---|
| PBS:Adipic Acid (90:10) + 2 wt % Unithox ® | 58.35 | 27.01 |
| PBS:Adipic Acid (85:15) + 2 wt % Unithox ® | 52.66 | 26.77 |
| Polypropylene | 128.1 | 93.9 |

Table 3 lists the results of the mechanical properties testing. As these results demonstrate, the nonwoven materials of the present invention are approximately as strong as the current polypropylene lines, but also much softer.

TABLE 3

Mechanical Properties

| | Control-0.5 osy polypropylene spunbond | 0.8 osy PBS:Adipic Acid:Unithox blend |
|---|---|---|
| MD % Elongation @ Peak Load | 27.36 | 24.86 |
| Cup Crush (grams) | 30 | 5 |

The softness of these nonwovens is due to the unique structure of the nonwoven material fibers. Each fiber contains a number of protrusions radiating out from the surface. These protrusions are, in some cases, like fibrils and, in others, are like a roughness on the surface. These protrusions lead to increased fiber entanglements, enhancing strength, and the small fibrils contribute to the fine fiber softness.

Table 4 gives the results for the fluid management properties of the nonwoven materials of the present invention. As the table demonstrates, the nonwoven materials of the present invention have a much faster intake time than the control surfactant-treated polypropylene spunbond liner. With subsequent insults, the surfactant begins to wash off the treated diaper liner and the intake times rise significantly. The permanently hydrophilic surface of the nonwoven material of the present invention remains permanently wettable, so that while intake times increase, they remain much lower than those for the polypropylene liner.

One of the most significant tests for skin dryness is how the material behaves in a TEWL test, which measures skin dryness when covered with a diaper insulted with saline. The lower TEWL value demonstrated by the nonwoven material of the present invention indicates an improvement in skin dryness.

TABLE 4

Fluid Management Properties

| | Control-0.5 osy polypropylene spunbond | 0.8 osy PBS:Adipic Acid:Unithox blend |
|---|---|---|
| FIFE - 1st Insult Time (sec) | 28.03 | 28.00 |
| FIFE - 2nd Insult Time (sec) | 83.30 | 57.03 |
| FIFE - 3rd Insult Time (sec) | 94.98 | 59.76 |
| TEWL (g/m$^2$) | 22.1 | 18.9 |

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A method of forming a multi-component fiber comprising:
   extruding a thermoplastic composition blend; and
   spinning the extruded thermoplastic composition blend into a continuous multi-component fiber;
   wherein the multi-component fiber exhibits an apparent viscosity value at a temperature of about 170° C. and a shear rate of about 1000 seconds$^{-1}$ that is between about 5 Pascal seconds and about 200 Pascal seconds.

2. The method of claim 1, wherein the thermoplastic composition blend comprises:
   a. an aliphatic polyester polymer selected from the group consisting of a polybutylene succinate polymer, a polybutylene succinate-co-adipate polymer, a polycaprolactone polymer, a mixture of such polymers, or a copolymer of such polymers, wherein the aliphatic polyester polymer exhibits a weight average molecular weight that is between about 10,000 to about 2,000,000, wherein the aliphatic polyester polymer is present in the thermoplastic composition in a weight amount that is between about 40 to less than 100 weight percent;
   b. a multicarboxylic acid having a total of carbon atoms that is less than about 30, wherein the multicarboxylic acid is present in the thermoplastic composition in a weight amount that is between greater than 0 weight percent to about 30 weight percent; and
   c. a wetting agent, which exhibits a hydrophilic-lipophilic balance ratio that is between about 10 to about 40, in a weight amount that is greater than 0 to about 25 weight percent, wherein all weight percents are based on the total weight amount of the aliphatic polyester polymer, the multicarboxylic acid, and the wetting agent present in the thermoplastic composition.

3. The method of claim 2, wherein the aliphatic polyester polymer is a polybutylene succinate polymer.

4. The method of claim 2, wherein the aliphatic polyester polymer is a polybutylene succinate-co-adipate polymer.

5. The method of claim 2, wherein the aliphatic polyester polymer is a polycaprolactone polymer.

6. The method of claim 2, wherein the aliphatic polyester polymer is present in the thermoplastic composition in a weight amount that is between about 50 weight percent to about 95 weight percent.

7. The method of claim 6, wherein the aliphatic polyester polymer is present in the thermoplastic composition in a weight amount that is between about 60 weight percent to about 90 weight percent.

8. The method of claim 2, wherein the multicarboxylic acid is selected from the group consisting of succinic acid, glutaric acid, adipic acid, pimelic acid, suberic acid, azelaic acid, sebacic acid, and a mixture of such acids.

9. The method of claim 8, wherein the multicarboxylic acid is selected from the group consisting of glutaric acid, adipic acid, and suberic acid.

10. The method of claim 2, wherein the multicarboxylic acid is present in the thermoplastic composition in a weight amount that is between about 1 weight percent to about 30 weight percent.

11. The method of claim 10, wherein the multicarboxylic acid is present in the thermoplastic composition in a weight amount that is between about 5 weight percent to about 25 weight percent.

12. The method of claim 2, wherein the multicarboxylic acid has a total of carbon atoms that is between about 4 to about 30.

13. The method of claim 2, wherein the wetting agent exhibits a hydrophilic-lipophlic balance ratio that is between about 10 to about 20.

14. The method of claim 2, wherein the wetting agent is present in the thermoplastic composition in a weight amount that is between about 0.5 weight percent to about 20 weight percent.

15. The method of claim 2, wherein the wetting agent is present in the thermoplastic composition in a weight amount that is between about 1 weight percent to about 15 weight percent.

16. The method of claim 2, wherein the wetting agent is selected from the group consisting of ethoxylated alcohols, acid amide ethoxylates, and ethoxylated alkyl phenols.

17. The method of claim 2, wherein the aliphatic polyester polymer is present in the thermoplastic composition in a weight amount that is between about 50 weight percent to about 95 weight percent, the multicarboxylic acid is selected from the group consisting of succinic acid, glutaric acid, adipic acid, pimelic acid, suberic acid, azelaic acid, sebacic acid, and a mixture of such acids and is present in the thermoplastic composition in a weight amount that is between about 1 weight percent to about 30 weight percent, and the wetting agent is selected from the group consisting of ethoxylated alcohols, acid amide ethoxylates, and ethoxylated alkyl phenols and is present in the thermoplastic composition in a weight amount that is between about 0.5 weight percent to about 20 weight percent.

18. The method of claim 1, wherein the multi-component fiber exhibits an Advancing Contact Angle value that is less than about 70 degrees and a Receding Contact Angle value that is less than about 60 degrees.

19. A method of forming a multi-component fiber comprising:
- extruding a thermoplastic composition blend;
- spinning the extruded thermoplastic composition blend into a continuous multi-component fiber;
- cooling, solidifying and drawing the continuous multi-component fiber to an intermediate filament diameter;
- drawing the intermediate multi-component fiber at a temperature below its softening point to a desired finished fiber diameter; and
- cutting the finished multi-component fiber into desirable lengths to form short-cut or staple multi-component fibers;
- wherein the multi-component fiber exhibits an Apparent Viscosity value at a temperature of about 170° C. and a shear rate of about 1000 seconds$^{-1}$ that is between about 5 Pascal seconds and about 200 Pascal seconds.

20. The method of claim 19, wherein the thermoplastic composition blend comprises:
- a. an aliphatic polyester polymer selected from the group consisting of a polybutylene succinate polymer, a polybutylene succinate-co-adipate polymer, a polycaprolactone polymer, a mixture of such polymers, or a copolymer of such polymers, wherein the aliphatic polyester polymer exhibits a weight average molecular weight that is between about 10,000 to about 2,000,000, wherein the aliphatic polyester polymer is present in the thermoplastic composition in a weight amount that is between about 40 to less than 100 weight percent;
- b. a multicarboxylic acid having a total of carbon atoms that is less than about 30, wherein the multicarboxylic acid is present in the thermoplastic composition in a weight amount that is between greater than 0 weight percent to about 30 weight percent; and
- c. a wetting agent, which exhibits a hydrophilic-lipophilic balance ratio that is between about 10 to about 40, in a weight amount that is greater than 0 to about 25 weight percent, wherein all weight percents are based on the total weight amount of the aliphatic polyester polymer, the multicarboxylic acid, and the wetting agent present in the thermoplastic composition.

21. The method of claim 20, wherein the aliphatic polyester polymer is a polybutylene succinate polymer.

22. The method of claim 20, wherein the aliphatic polyester polymer is a polybutylene succinate-co-adipate polymer.

23. The method of claim 20, wherein the aliphatic polyester polymer is a polycaprolactone polymer.

24. The method of claim 20, wherein the aliphatic polyester polymer is present in the thermoplastic composition in a weight amount that is between about 50 weight percent to about 95 weight percent.

25. The method of claim 24, wherein the aliphatic polyester polymer is present in the thermoplastic composition in a weight amount that is between about 60 weight percent to about 90 weight percent.

26. The method of claim 20, wherein the multicarboxylic acid is selected from the group consisting of succinic acid, glutaric acid, adipic acid, pimelic acid, suberic acid, azelaic acid, sebacic acid, and a mixture of such acids.

27. The method of claim 26, wherein the multicarboxylic acid is selected from the group consisting of glutaric acid, adipic acid, and suberic acid.

28. The method of claim 20, wherein the multicarboxylic acid is present in the thermoplastic composition in a weight amount that is between about 1 weight percent to about 30 weight percent.

29. The method of claim 28, wherein the multicarboxylic acid is present in the thermoplastic composition in a weight amount that is between about 5 weight percent to about 25 weight percent.

30. The method of claim 20, wherein the multicarboxylic acid has a total of carbon atoms that is between about 4 to about 30.

31. The method of claim 20, wherein the wetting agent exhibits a hydrophilic-lipophilic balance ratio that is between about 10 to about 20.

32. The method of claim 20, wherein the wetting agent is present in the thermoplastic composition in a weight amount that is between about 0.5 weight percent to about 20 weight percent.

33. The method of claim 20, wherein the wetting agent is present in the thermoplastic composition in a weight amount that is between about 1 weight percent to about 15 weight percent.

34. The method of claim 20, wherein the wetting agent is selected from the group consisting of ethoxylated alcohols, acid amide ethoxylates, and ethoxylated alkyl phenols.

35. The method of claim 20, wherein the aliphatic polyester polymer is present in the thermoplastic composition in a weight amount that is between about 50 weight percent to about 95 weight percent, the multicarboxylic acid is selected from the group consisting of succinic acid, glutaric acid, adipic acid, pimelic acid, suberic acid, azelaic acid, sebacic acid, and a mixture of such acids and is present in the thermoplastic composition in a weight amount that is between about 1 weight percent to about 30 weight percent, and the wetting agent is selected from the group consisting of ethoxylated alcohols, acid amide ethoxylates, and ethoxylated alkyl phenols and is present in the thermoplastic composition in a weight amount that is between about 0.5 weight percent to about 20 weight percent.

36. The method of claim 19, wherein the multi-component fiber exhibits an Advancing Contact Angle value that is less than about 70 degrees and a Receding Contact Angle value that is less than about 60 degrees.

37. A method of making a biodegradable thermoplastic composition comprising:
- mixing together an aliphatic polyester polymer, a multicarboxylic acid, and a wetting agent to form a thermoplastic composition dry mixture, and
- melt blending the aliphatic polyester polymer, the multicarboxylic acid, and the wetting agent such that an essentially homogeneous melted mixture is formed.

38. The method of claim 37, further comprising agitating the thermoplastic composition dry mixture such that an essentially homogeneous dry mixture is formed.

39. The method of claim 37, wherein the thermoplastic composition blend comprises:
   a. an aliphatic polyester polymer selected from the group consisting of a polybutylene succinate polymer, a polybutylene succinate-co-adipate polymer, a polycaprolactone polymer, a mixture of such polymers, or a copolymer of such polymers, wherein the aliphatic polyester polymer exhibits a weight average molecular weight that is between about 10,000 to about 2,000,000, wherein the aliphatic polyester polymer is present in the thermoplastic composition in a weight amount that is between about 40 to less than 100 weight percent;
   b. a multicarboxylic acid having a total of carbon atoms that is less than about 30, wherein the multicarboxylic acid is present in the thermoplastic composition in a weight amount that is between greater than 0 weight percent to about 30 weight percent; and
   c. a wetting agent, which exhibits a hydrophilic-lipophilic balance ratio that is between about 10 to about 40, in a weight amount that is greater than 0 to about 25 weight percent, wherein all weight percents are based on the total weight amount of the aliphatic polyester polymer, the multicarboxylic acid, and the wetting agent present in the thermoplastic composition.

40. The method of claim 37, wherein the thermoplastic composition exhibits an Apparent Viscosity value at a temperature of about 170° C. and a shear rate of about 1000 seconds$^{-1}$ that is between about 5 Pascal seconds and about 200 Pascal seconds.

41. The method of claim 37, wherein the thermoplastic composition exhibits an Advancing Contact Angle value that is less than about 70 degrees and a Receding Contact Angle value that is less than about 60 degrees.

42. The method of claim 37, wherein the method is operated at a shear rate that is between about 100 seconds$^{-1}$ to about 50000 seconds$^{-1}$.

43. The method of claim 37, wherein the method is operated at a shear rate that is between about 500 seconds$^{-1}$ to about 5000 seconds$^{-1}$.

44. The method of claim 37, wherein the method is operated at a shear rate that is between about 1000 seconds$^{-1}$ to about 3000 seconds$^{-1}$.

45. The method of claim 37, wherein the method is operated at a shear rate that is at about 1000 seconds$^{-1}$.

46. The method of claim 37, wherein the method is operated at a processing temperature that is between about 50° C. to about 500° C.

47. The method of claim 37, wherein the method is operated at a processing temperature that is between about 75° C. to about 300° C.

48. The method of claim 37, wherein the method is operated at a processing temperature that is between about 100° C. to about 250° C.

* * * * *

UNITED STATES PATENT AND TRADEMARK OFFICE
CERTIFICATE OF CORRECTION

PATENT NO. : 6,245,831 B1
DATED : June 12, 2001
INVENTOR(S) : Fu-Jya Daniel Tsai and Brigitte C. Wertheim It is certified that error appears in the above-identified patent and that said Letters Patent is hereby corrected as shown below:

<u>Title page, Item [54] and Column 1, lines 1-4,</u>
Delete "DISPOSABLE ARTICLES HAVING BIODEGRADABLE NONWOVENS WITH IMPROVED FLUID MANAGEMENT PROPERTIES" and substitute
-- METHODS FOR MAKING A THERMOPLASTIC COMPOSITION AND FIBERS INCLUDING SAME --.

<u>Column 13,</u>
Line 52, delete "11" and substitute -- II --.

Signed and Sealed this

Second Day of July, 2002

Attest:

Attesting Officer

JAMES E. ROGAN
*Director of the United States Patent and Trademark Office*